United States Patent
Ohlbach et al.

(10) Patent No.: US 6,828,457 B2
(45) Date of Patent: Dec. 7, 2004

(54) METHOD FOR REDUCING THE CONTENT OF AN UNSATURATED AMINE IN A MIXTURE CONTAINING AN AMINE AND A NITRILE

(75) Inventors: Frank Ohlbach, Düsseldorf (DE); Christoph Benisch, Eppelheim (DE); Hermann Luyken, Ludwigshafen (DE); Andreas Ansmann, Wiesloch (DE); Rolf-Hartmuth Fischer, Heidelberg (DE); Johann-Peter Melder, Böhl-Iggelheim (DE); Peter Bassler, Viernheim (DE); Stefan Maixner, Schwetzingen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/432,385
(22) PCT Filed: Nov. 29, 2001
(86) PCT No.: PCT/EP01/13954
§ 371 (c)(1), (2), (4) Date: May 21, 2003
(87) PCT Pub. No.: WO02/44135
PCT Pub. Date: Jun. 6, 2002

(65) Prior Publication Data
US 2004/0030174 A1 Feb. 12, 2004

(30) Foreign Application Priority Data
Nov. 30, 2000 (DE) .......... 100 59 716

(51) Int. Cl.⁷ .......... C07C 253/34
(52) U.S. Cl. .......... 558/452; 564/498
(58) Field of Search .......... 558/452; 564/498

(56) References Cited
U.S. PATENT DOCUMENTS

| | | | |
|---|---|---|---|
| 2,208,598 A | 7/1940 | Rigby et al. | |
| 2,762,835 A | 11/1956 | Swerdloff et al. | |
| 3,696,153 A | 10/1972 | Kershaw et al. | |
| 4,601,859 A | 7/1986 | Galle et al. | |
| 5,192,399 A | * 3/1993 | Sieja | 203/36 |
| 6,147,208 A | 11/2000 | Achhammer et al. | |
| 6,169,199 B1 | 1/2001 | Rehfinger et al. | |
| 6,252,115 B1 | 6/2001 | Luyken et al. | |

FOREIGN PATENT DOCUMENTS

| | | |
|---|---|---|
| DE | 848 654 | 9/1952 |
| DE | 954 416 | 12/1956 |
| DE | 42 35 466 | 4/1994 |
| EP | 497 333 | 8/1992 |
| EP | 502 439 | 9/1992 |
| EP | 641 315 | 3/1995 |
| WO | 93/14064 | 7/1993 |
| WO | 93/16984 | 9/1993 |

OTHER PUBLICATIONS

XP–001064740 Koskikallio, Acta Chemica Scandinavica, 23, 1477–1489, 1969.
Ind. Org. Chemie, 3 1988, 266, Weissermel.

* cited by examiner

Primary Examiner—Fiona T. Powers
(74) Attorney, Agent, or Firm—Keil & Weinkauf

(57) ABSTRACT

A process is provided for reducing the content of a monounsaturated aliphatic amine (III) in a mixture (IV) containing an aminonitrile (I) or a diamine (II), or mixtures thereof, and the amine (III), wherein a) the mixture (IV) is reacted with an anionic nucleophile (V),
   which contains a nucleophilic atom selected from the group comprising oxygen, nitrogen and sulfur,
   which is capable of taking up an H⁺ ion to form an acid with a $pK_a$ ranging from 7 to 11, measured in water at 25° C., and
   which has a relative nucleophilicity, measured in methyl perchlorate/methanol at 25° C.,
   ranging from 3.4 to 4.7 when oxygen is the nucleophilic atom,
   ranging from 4.5 to 5.8 when nitrogen is the nucleophilic atom, and
   ranging from 5.5 to 6.8 when sulfur is the nucleophilic atom,
   in an amount ranging from 0.01 to 10 mol per mole of amine (III) in the mixture (IV), to give a mixture (VI), and b) the aminonitrile (I) or the diamine (II), or mixtures thereof, are distilled from the mixture (VI) at a temperature ranging from 50 to 170° C. and a pressure ranging from 0.5 to 100 kPa.

12 Claims, No Drawings

METHOD FOR REDUCING THE CONTENT OF AN UNSATURATED AMINE IN A MIXTURE CONTAINING AN AMINE AND A NITRILE

The present invention relates to a process for reducing the content of a monounsaturated aliphatic amine (III) in a mixture (IV) containing an aminonitrile (I) or a diamine (II), or mixtures thereof, and the amine (III), wherein a) the mixture (IV) is reacted with an anionic nucleophile (V),
   which contains a nucleophilic atom selected from the group comprising oxygen, nitrogen and sulfur,
   which is capable of taking up an H$^+$ ion to form an acid with a pK$_a$ ranging from 7 to 11, measured in water at 25° C., and
   which has a relative nucleophilicity, measured in methyl perchlorate/methanol at 25° C.,
   ranging from 3.4 to 4.7 when oxygen is the nucleophilic atom,
   ranging from 4.5 to 5.8 when nitrogen is the nucleophilic atom, and
   ranging from 5.5 to 6.8 when sulfur is the nucleophilic atom,
   in an amount ranging from 0.01 to 10 mol per mole of amine (III) in the mixture (IV), to give a mixture (VI), and
b) the aminonitrile (I) or the diamine (II), or mixtures thereof, are distilled from the mixture (VI) at a temperature ranging from 50 to 170° C. and a pressure ranging from 0.5 to 100 kPa.

Mixtures containing an aminonitrile or a diamine, or mixtures thereof, and an unsaturated amine—an unsaturated amine being understood in terms of the present invention as meaning a cyclic or linear compound containing at least one carbon-nitrogen double bond or a compound capable of forming at least one carbon-nitrogen double bond, for example by an elimination reaction—are conventionally obtained in the partial hydrogenation of dinitriles to aminonitriles or a mixture of aminonitriles and diamines, or in the complete hydrogenation of dinitriles to diamines.

The partial hydrogenation of adipodinitrile (ADN) with the simultaneous production of hexamethylenediamine (HMD) and 6-aminocapronitrile (ACN), and the complete hydrogenation of ADN to HMD, in the presence of a catalyst based on a metal such as nickel, cobalt, iron, rhodium or ruthenium, is generally known e.g. from K. Weissermel, H.-J. Arpe, Industrielle Organische Chemie (Industrial Organic Chemistry), 3rd edition, VCH Verlagsgesellschaft mbH, Weinheim, 1988, page 266, U.S. Pat. No. 4,601,859, U.S. Pat. No. 2,762,835, U.S. Pat. No. 2,208,598, DE-A 848 654, DE-A 954 416, DE-A 42 35 466, U.S. Pat. No. 3,696,153, DE-A 19500222, WO-A-92/21650 and DE-A-19548289.

The byproducts formed are, inter alia, azepine derivatives such as N-(2-azepano)-1,6-diaminohexane, N-(2-azepano)-6-aminocapronitrile and, in particular, 2-aminoazepan and tetrahydroazepine (THA).

These azepine derivatives, which cause coloration and impair the product properties and are therefore unwanted impurities in the aminonitriles and diamines conventionally used for the manufacture of synthetic fibers or engineering plastics, can be separated from the aminonitriles, diamines or mixtures thereof only at considerable expense.

EP-A-497333 describes the separation of aliphatic aminonitriles or aliphatic diamines from mixtures containing an aliphatic aminonitrile or aliphatic diamine and a cyclic, monounsaturated aliphatic amine by the addition of bases, the base being used in stoichiometric excess relative to the cyclic, monounsaturated aliphatic amine. Bases recommended for this separation are alkali metal hydroxides, alkaline earth metal hydroxides, tetraalkylammonium hydroxide, alkali metal alkoxides and alkaline earth metal alkoxides.

The disadvantage of this process is a simultaneous polymerization of valuable product which leads to an appreciable loss of valuable product and to unwanted deposits in the apparatuses and machines used for carrying out the process.

It is an object of the present invention to provide a process for reducing the content of a monounsaturated aliphatic amine in a mixture containing an aminonitrile or a diamine, or mixtures thereof, and a monounsaturated aliphatic amine, in a technically simple and economic manner which avoids said disadvantages.

We have found that this object is achieved by the process defined at the outset.

Suitable aminonitriles (I) are compounds containing one or more, such as two, three or four, nitrile groups, preferably one nitrile group, especially compounds containing at least one nitrile group which is located adjacent to an aliphatic carbon atom carrying one or two, preferably two, hydrogen atoms, or mixtures of such aminonitriles.

Suitable aminonitriles (I) are compounds containing one or more, such as two, three or four, amino groups, preferably one amino group, especially compounds containing at least one amino group which is located adjacent to an aliphatic carbon atom carrying one or two, preferably two, hydrogen atoms, or mixtures of such aminonitriles. Particularly preferred aminonitriles are those containing a terminal amino group, i.e. an amino group located at the end of an alkyl chain.

The aminonitrile (I) is preferably based on an alkyl skeleton.

In a preferred embodiment, the aminonitrile (I) has from 4 to 12 carbon atoms.

Suitable aminonitriles (I) are preferably selected from the group comprising 4-aminobutyronitrile, 5-aminovaleronitrile, 2-methyl-5-aminovaleronitrile, 6-aminocapronitrile and 12-aminododecanenitrile, especially 6-aminocapronitrile.

Such aminonitriles can be prepared in a manner known per se.

6-Aminocapronitrile can be obtained by the partial catalytic hydrogenation of ADN with a gas containing molecular hydrogen to give mixtures containing HMD and ACN.

Catalysts which can advantageously be used in this hydrogenation are those based on a metal selected from the group comprising ruthenium, rhodium, nickel, cobalt and, preferably, iron, it being possible for the catalysts to contain other elements as promoters. In the case of iron-based catalysts, suitable promoters are especially one or more, such as two, three, four or five, elements selected from the group comprising aluminum, silicon, zirconium, titanium and vanadium.

Such catalysts and the process conditions for said reaction are described for example in WO-A-96/20166, DE-A-19636768 and DE-A-19646436.

Suitable diamines (II) are compounds containing two or more, such as two, three or four, amino groups, preferably two amino groups, especially compounds containing at least two amino groups which are located adjacent to an aliphatic carbon atom carrying one or two, preferably two, hydrogen atoms, and particularly preferably diamines containing terminal amino groups, i.e. amino groups located at the end of an alkyl chain, or mixtures of such diamines.

The diamine (II) is preferably based on an alkyl skeleton.

In a preferred embodiment, the diamine (II) has from 4 to 12 carbon atoms.

Suitable diamines (II) are preferably selected from the group comprising 1,4-diaminobutane, 1,5-diaminopentane, 2-methyl-1,5-diaminopentane, 1,6-diaminohexane (HMD) and 1,12-diaminododecane.

Such diamines can be prepared in manner known per se.

HMD can be obtained by the partial catalytic hydrogenation of ADN with a gas containing molecular hydrogen to give mixtures containing HMD and ACN, or by the complete hydrogenation of ADN with a gas containing molecular hydrogen.

Catalysts which can advantageously be used in this hydrogenation are those based on a metal selected from the group comprising ruthenium, rhodium, nickel, cobalt and, preferably, iron, it being possible for the catalysts to contain other elements as promoters. In the case of iron-based catalysts, suitable promoters are especially one or more, such as two, three, four or five, elements selected from the group comprising aluminium, silicon, zirconium, titanium and vanadium.

Such catalysts and the process conditions for said reactions can be found for example in the publications already cited above.

Suitable amines (III) are cyclic or linear compounds containing at least one carbon-nitrogen double bond or a compound capable of forming at least one carbon-nitrogen double bond, for example by an elimination reaction, or mixtures of such compounds.

The amine (III) used can advantageously be a compound of the formula

R¹—(CH₂)ₙ—CH=N—(CH₂)ₘ—R² in which n and m independently of one another are 1, 2, 3, 4, 5, 6, 7, 8, 9, 10, 11 or 12, preferably 4, 5 or 6, and R¹ and R² independently of one another are —CN or —NH₂, or of the formula

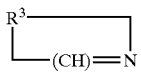

in which R³ is an alkenyl radical having 3, 4, 5, 6, 7, 8, 9, 10 or 11 carbon atoms belonging to the ring system.

In a preferred embodiment, the amine (III) used is selected from the group comprising dihydropyrrole, tetrahydropyridine, 3-methyltetrahydropyridine, tetrahydroazepine and monounsaturated cyclododecylamines, or mixtures thereof.

These amines (III) can be present in the mixture (IV) as individual compounds or as adducts, for example with a nitrile (I), especially an aminonitrile, said adducts also being referred to as amines (III) in terms of the present invention.

Such amines (III) and processes for their preparation are generally known. Thus tetrahydroazepine can be obtained in mixtures (IV) in the partial catalytic hydrogenation of ADN with a gas containing molecular hydrogen to give mixtures containing HMD and ACN, normally in amounts of 1 to 10,000 ppm, based on the mixture, by the processes described for the preparation of ACN.

Also, said amines (III) can be formed by the oxidation of amines such as HMD, for example with gases containing molecular oxygen.

In a preferred embodiment, the mixture (IV) used can be the reaction product obtained from the partial catalytic hydrogenation, such as gas phase hydrogenation or liquid phase hydrogenation, of dinitriles, especially ADN, with a gas containing molecular hydrogen, in the presence of a catalyst such as a suspension catalyst or fixed bed catalyst, said reaction product containing ACN as the aminonitrile (I), HMD as the diamine (II) and tetrahydroazepine as the amine (III) in the case where ADN is the starting compound, it being possible, if desired, for all or part of any solvent previously used in the hydrogenation to be separated off. According to previous observations, it can be advantageous for a catalyst used in the hydrogenation to be separated off before the mixture (IV) is used in the process according to the invention.

In a preferred embodiment, the mixture (IV) used can be the reaction product obtained from the complete catalytic hydrogenation, such as gas phase hydrogenation or liquid phase hydrogenation, of dinitriles, especially ADN, with a gas containing molecular hydrogen, in the presence of a catalyst such as a suspension catalyst or fixed bed catalyst, said reaction product containing HMD as the diamine (II) and tetrahydroazepine as the amine (III) in the case where ADN is the starting compound, it being possible, if desired, for all or part of any solvent previously used in the hydrogenation to be separated off. According to previous observations, it can be advantageous for a. catalyst used in the hydrogenation to be separated off before the mixture (IV) is used in the process according to the invention.

According to the invention, an anionic nucleophile (V) is added to the mixture (IV).

The term "anionic" is understood in terms of the present invention as meaning that in total the nucleophile (V) carries one or more, such as two or three, negative charges, preferably one negative charge.

The term "nucleophilic" is understood in terms of the present invention as meaning the ability of a compound, as described in Koskikallo, Acta Chem. Scand. 23 (1969) pages 1477–1489, to displace the perchlorate group from methyl perchlorate in methanolic solution at 25° C., the remaining methyl group being bonded to the compound (V) via a nucleophilic atom of the compound (V).

A suitable nucleophilic atom of the compound (V) is an atom selected from the group comprising nitrogen, oxygen and sulfur, preferably nitrogen or oxygen.

According to the invention, the compound (V) is capable of taking up an H⁺ ion to form an acid with a pK$_a$ ranging from 7 to 11, preferably from 8 to 10.5, measured in water at 25° C.

According to the invention, the relative nucleophilicity of the compound (V), measured in methyl perchlorate/methanol at 25° C. according to Koskikallo, Acta Chem. Scand. 23 (1969) pages 1477–1489, and determined as on pages 1487–1488, ranges from 3.4 to 4.7, preferably from 3.6 to 4.6, when oxygen is the nucleophilic atom, from 4.5 to 5.8, preferably from 4.8 to 5.7, when nitrogen is the nucleophilic atom, and from 5.5 to 6.8, preferably from 5.8 to 6.7, when sulfur is the nucleophilic atom.

When oxygen is the nucleophilic atom of (V), phenates are advantageously suitable, it being possible for the aromatic ring system of the phenate to be monosubstituted or polysubstituted, such as disubstituted or trisubstituted, for example by a $C_1$- to $C_4$-alkyl group such as methyl, ethyl, n-propyl, i-propyl, n-butyl, i-butyl, s-butyl or t-butyl, by a halogen such as fluorine, chlorine, bromine or iodine, by a nitro group, by an ester group, by a carbonyl group or by an amino group.

When nitrogen is the nucleophilic atom of (V), suitable compounds are advantageously those containing the structural unit

where $R^4$ is the radical of an organic aliphatic, arylaliphatic or aromatic acid, preferably a carboxylic acid or sulfonic acid group, it being possible for the radical $R^4$ to be substituted as already described above for phenate, and $R^5$ is the radical of an organic aliphatic, arylaliphatic or aromatic acid, preferably a carboxylic acid or sulfonic acid group, hydrogen or a $C_1$- to $C_4$-alkyl group such as methyl, ethyl, n-propyl, i-propyl, n-butyl, i-butyl, s-butyl or t-butyl, it being possible for the radical $R^5$ to be substituted as already described above for phenate, it being possible for $R^4$ and $R^5$ to be coupled together other than by the nitrogen mentioned in the above formula, for example via an alkylene, alkylarylene or arylene bridge, preferably via an arylene bridge.

In a preferred embodiment, the nucleophile (V) used can be a lactam anion of the general formula

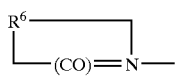

in which $R^6$ is an alkylene radical having 3, 4, 5, 6, 7, 8, 9, 10 or 11 carbon atoms belonging to the ring system, it being possible for the radical $R^6$ to be substituted as already described above for phenate.

In a preferred embodiment, the nucleophile (V) used can be a caprolactam anion.

In another particularly preferred embodiment, the nucleophile (V) used can be a benzenesulfonamide anion.

In another particularly preferred embodiment, the nucleophile (V) used can be a phthalimide anion.

In another particularly preferred embodiment, the nucleophile (V) used can be phenate.

For compensation of the negative charge on the anionic nucleophile (V), the latter can be used together with one or more cations preferably selected from the group comprising lithium, sodium, potassium, rubidium, cesium, magnesium and calcium, especially comprising lithium, sodium, potassium, magnesium and calcium and particularly preferably comprising sodium and potassium.

According to the invention, the nucleophile (V) is added to the mixture (IV) in an amount ranging from 0.01 to 10 mol per mole of amine (III) in the mixture (IV).

Advantageously, the amount of nucleophile (V) can be at least 0.05 mol and especially 0.1 mol per mole of amine (III) in the mixture (IV).

Advantageously, the amount of nucleophile (V) can be at most 1 mol, especially at most 0.8 mol and particularly preferably at most 0.5 mol per mole of amine (III) in the mixture (IV).

The nucleophile (V) can be added to the mixture (IV) in a manner known per se, for example in conventional mixing apparatuses such as tanks, product lines and mixing devices, to give a mixture (VI).

The nucleophile (V) can be added to the mixture (IV) before the mixture (VI) is introduced into a distillation device for separation of the nitrile (I) from the mixture (VI). Periods of 5 to 120 minutes, especially of 10 to 60 minutes, have proved advantageous as average contact times between the mixture (IV) and the nucleophile (V) before introduction into a distillation device, suitable temperatures advantageously ranging from 50 to 170° C.

Another possibility is to introduce the mixture (IV) and the nucleophile (V) separately into such a device and to carry out the reaction of the mixture (IV) with the nucleophile (V) and the separation of the nitrile (I) from the mixture (VI) in one process step, it being possible for the nucleophile (V) to be introduced onto the top, over the entire height onto one of the separation stages or into the bottom of the distillation device.

According to the invention, the nitrile (I) is distilled from the mixture (VI) at a temperature ranging from 50 to 170° C., preferably from 70 to 150° C., and a pressure ranging from 0.5 to 100 kPa, preferably from 0.5 to 10 kPa.

Suitable apparatuses are those conventionally used for distillation, for example the ones described in Kirk-Othmer, Encyclopedia of Chemical Technology, 3rd ed., vol. 7, John Wiley & Sons, New York, 1979, pages 870–881, such as sieve-plate columns, bubble-cap columns, packed columns or columns with a side discharge, or variants of such apparatuses in terms of process technology.

The distillation can be carried out in several columns, such as 2 or 3 columns, and advantageously in a single column.

Aminonitriles and diamines are precursors for the preparation of industrially important polyamides such as nylon 6 or nylon 6.6.

EXAMPLES

Example 1

500 ml of 6-aminocapronitrile with a tetrahydroazepine (THA) content of 300 ppm by weight were treated with 30 mol %, based on THA, of potassium phthalimide and distilled at 96° C. and 0.5 kPa (bottom temperature 110–115° C.) over a distillation column 1 m in length containing V2A wire-gauze rings. After 450 ml had distilled over, the distillation was stopped. 6 ppm of THA were found in the distillate.

Example 2

500 ml of 6-aminocapronitrile with a THA content of 1% by weight were treated with 50 mol %, based on THA, of potassium phthalimide and distilled at 96° C. and 0.5 kPa (bottom temperature 110–115° C.) over a distillation column 1 m in length containing V2A wire-gauze rings. After 450 ml had distilled over, the distillation was stopped. 0.09% by weight of THA was found in the distillate.

Example 3

For the continuous separation of THA from 6-aminocapronitrile, 6-aminocapronitrile with a THA content of 300 ppm by weight was pumped continuously into a 750 ml tank in which a suspension of potassium phthalimide in 6-aminocapronitrile with a THA content of 300 ppm by weight was being stirred at 65° C. The resulting potassium phthalimide content of the solution was 160–170 ppm by weight.

This solution was pumped continuously out of the tank into a 250 ml distillation flask, from which the ACN was distilled at 10 mbar and a bottom temperature of 118° C. over a column 30 cm in length containing V2A wire-gauze rings.

With a loading rate of 210 ml/h, a take-off/reflux ratio of 50:50 and a bottom discharge rate of 10 ml/h, 30 ppm by weight of THA were found in the distillate. The yield of 6-aminocapronitrile was 95%.

We claim:

1. A process for reducing the content of a monounsaturated aliphatic amine (III) in a mixture (IV) containing an aminonitrile (I) or a diamine (II), or mixtures thereof, and the amine (III), wherein a) the mixture (IV) is reacted with an anionic nucleophile (V), which contains a nucleophilic atom selected from the group consisting oxygen, nitrogen and sulfur, which is capable of taking up an $H^+$ ion to form an acid with a $pK_a$ ranging from 7 to 11, measured in water at 25° C., and which has a relative nucleophilicity, measured in methyl perchlorate/methanol at 25° C., ranging from 3.4 to 4.7 when oxygen is the nucleophilic atom, ranging from 4.5 to 5.8 when nitrogen is the nucleophilic atom, and ranging from 5.5 to 6.8 when sulfur is the nucleophilic atom, in an amount ranging from 0.01 to 10 mol per mole of amine (III) in the mixture (IV), to give a mixture (VI), and b) the aminonitrile (I) or the diamine (II), or mixtures thereof, are distilled from the mixture (VI) at a temperature ranging from 50 to 170° C. and a pressure ranging from 0.5 to 100 kPa.

2. A process as claimed in claim 1 wherein the aminonitrile (I) used is an aliphatic aminonitrile having from 4 to 12 C atoms.

3. A process as claimed in claim 1 wherein the aminonitrile (I) used is an aliphatic aminonitrile having from 4 to 12 C atoms selected from the group consisting 4-aminobutyronitrile, 5-aminovaleronitrile, 2-methyl-5-aminovaleronitrile, 6-aminocapronitrile and 12-aminododecanenitrile.

4. A process as claimed in claim 1 wherein the diamine (II) used is an aliphatic diamine having from 4 to 12 C atoms.

5. A process as claimed in claim 1 wherein the diamine (II) used is an aliphatic diamine having from 4 to 12 C atoms selected from the group consisting 1,4-diaminobutane, 1,5-diaminopentane, 2-methyl-1,5-diaminopentane, 1,6-diaminohexane and 1,12-diaminododecane.

6. A process as claimed in any of claims 1 to 5 wherein the amine (III) used is a compound selected from the group consisting dihydropyrrole, tetrahydropyridine, 3-methyltetrahydropyridine, tetrahydroazepine, 2-aminoazepan, N-(2-azepano)-1,6-diaminohexane, N-(2-azepano)-6-aminocapronitrile and monounsaturated cyclododecylamines.

7. A process as claimed in any of claims 1 to 6 wherein the nucleophile (V) used is a benzenesulfonamide anion.

8. A process as claimed in any of claims 1 to 7 wherein the nucleophile (V) used is a phthalimide anion.

9. A process as claimed in any of claims 1 to 8 wherein the nucleophile (V) used is phenate.

10. A process as claimed in any of claims 1 to 9 wherein the nucleophile (V) used is a lactam anion of the general formula

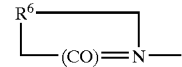

in which $R^6$ is an alkylene radical having 3, 4, 5, 6, 7, 8, 9, 10 or 11 carbon atoms belonging to the ring system.

11. A process as claimed in any of claims 1 to 10 wherein the nucleophile (V) used is a caprolactam anion.

12. A process as claimed in any of claims 1 to 11 wherein the anionic nucleophile (V) is used together with a cation selected from the group consisting lithium, sodium, potassium, magnesium and calcium.

* * * * *